United States Patent
Rodriguez

(10) Patent No.: US 9,308,001 B2
(45) Date of Patent: Apr. 12, 2016

(54) VERTEBRAL CAVITATION SURGICAL TOOL

(76) Inventor: Carlos Andres Rodriguez, Atlanta, GA (US)

( * ) Notice: Subject to any disclaimer, the term of this patent is extended or adjusted under 35 U.S.C. 154(b) by 393 days.

(21) Appl. No.: 13/421,067

(22) Filed: Mar. 15, 2012

(65) Prior Publication Data

US 2012/0239072 A1    Sep. 20, 2012

Related U.S. Application Data

(60) Provisional application No. 61/454,022, filed on Mar. 18, 2011, provisional application No. 61/494,624, filed on Jun. 8, 2011.

(51) Int. Cl.
| | | |
|---|---|---|
| A61B 17/14 | (2006.01) | |
| A61B 17/16 | (2006.01) | |
| A61B 17/32 | (2006.01) | |
| A61B 17/34 | (2006.01) | |

(52) U.S. Cl.
CPC ......... *A61B 17/1617* (2013.01); *A61B 17/1671* (2013.01); *A61B 17/32002* (2013.01); *A61B 17/320016* (2013.01); *A61B 17/3421* (2013.01)

(58) Field of Classification Search
USPC .......... 606/78, 79, 80, 83, 84, 86 A, 86 R, 92, 606/167, 170, 180, 185; 604/93.01, 117, 604/264, 272, 273, 274, 506; 128/898
See application file for complete search history.

(56) References Cited

U.S. PATENT DOCUMENTS

| | | | |
|---|---|---|---|
| 5,160,323 A | | 11/1992 | Andrew |
| 5,195,505 A | * | 3/1993 | Josefsen ...................... 600/204 |
| 5,199,419 A | * | 4/1993 | Remiszewski et al. ........ 600/204 |
| 5,245,987 A | * | 9/1993 | Redmond et al. ............. 600/204 |
| 5,381,788 A | * | 1/1995 | Matula et al. ................. 600/214 |
| 5,456,695 A | * | 10/1995 | Herve Dallemagne ....... 606/207 |
| 5,514,157 A | * | 5/1996 | Nicholas et al. .............. 606/206 |
| 5,554,101 A | * | 9/1996 | Matula et al. ................. 600/214 |
| 5,722,935 A | * | 3/1998 | Christian ...................... 600/214 |
| 5,928,239 A | | 7/1999 | Mirza |
| 6,425,887 B1 | | 7/2002 | McGuckin et al. |
| 6,592,559 B1 | | 7/2003 | Pakter et al. |

(Continued)

OTHER PUBLICATIONS

CareFusion, Jamshidi bone marrow biopsy products and Safe-T PLUS trays, 2010 (p. 6).*

*Primary Examiner* — Robert Lynch
(74) *Attorney, Agent, or Firm* — Allen D. Hertz, P.A.; Allen D. Hertz

(57) ABSTRACT

The instant invention describes a surgical tool for providing cavitations, or void spots, within the interior of body regions. The surgical tool is constructed and arranged to penetrate almost all interior body regions in which formation of a cavity or void space is necessary for diagnostic or treatment purposes. The surgical tool comprises an insertable member receiving structure sized and shaped to receive one or more insertable devices. The interior lumen of the insertable member receiving structure allows the insertable device to slide and/or rotate relative to the insertable member receiving structure and vice versa. At least one insertable member is a cavity forming device which has a plurality of cavity forming members constructed and arranged with spring-like characteristics for traversing between a cavity forming position and a non-cavity forming position. Upon traversal back to the cavity forming position, the displacement members retain their cavity forming structural configurations.

25 Claims, 27 Drawing Sheets

(56) References Cited

U.S. PATENT DOCUMENTS

| | | |
|---|---|---|
| 6,746,451 B2 | 6/2004 | Middleton et al. |
| 6,923,813 B2 | 8/2005 | Phillips et al. |
| 8,470,043 B2 * | 6/2013 | Schaller et al. ............ 623/17.16 |
| 2004/0267269 A1 | 12/2004 | Middleton et al. |
| 2005/0240193 A1 | 10/2005 | Layne et al. |
| 2007/0168041 A1 | 7/2007 | Kadiyala |
| 2008/0114364 A1 | 5/2008 | Goldin et al. |
| 2008/0140084 A1 * | 6/2008 | Osorio et al. ................... 606/94 |
| 2009/0138043 A1 | 5/2009 | Kohm |
| 2010/0076445 A1 | 3/2010 | Pagano |
| 2010/0174267 A1 | 7/2010 | McGuckin, Jr. |
| 2010/0185161 A1 | 7/2010 | Pellegrino et al. |

* cited by examiner

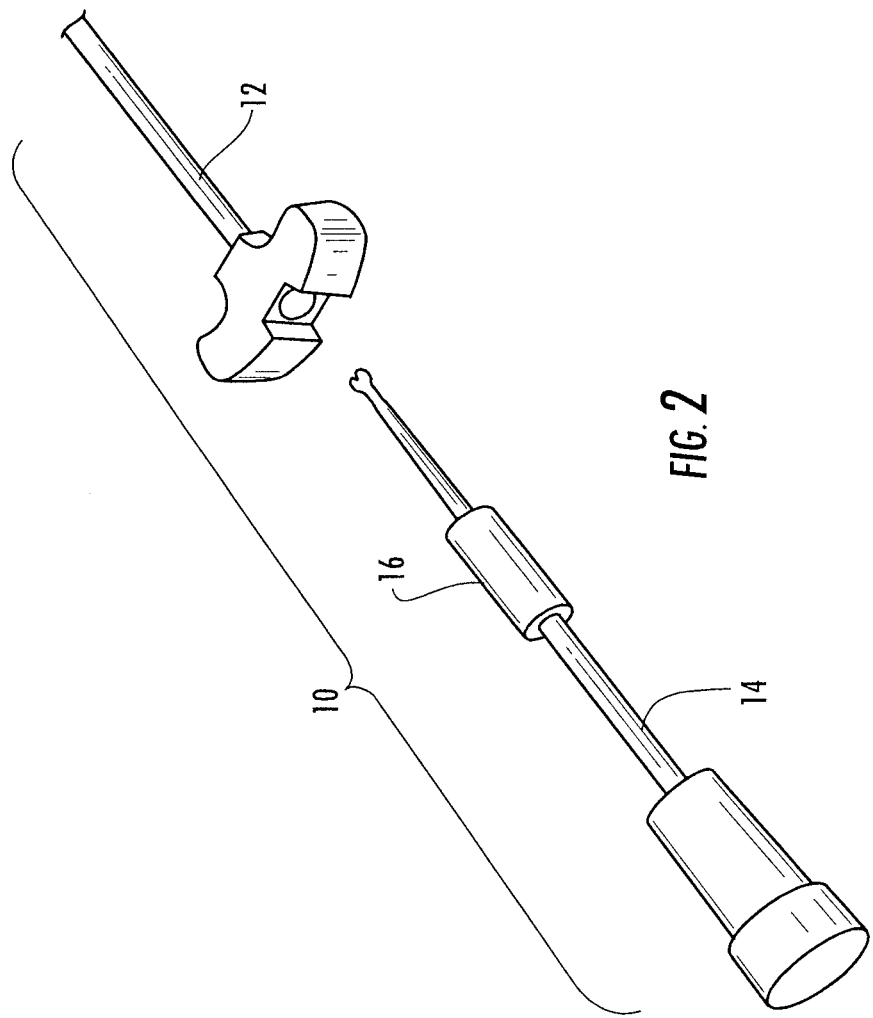

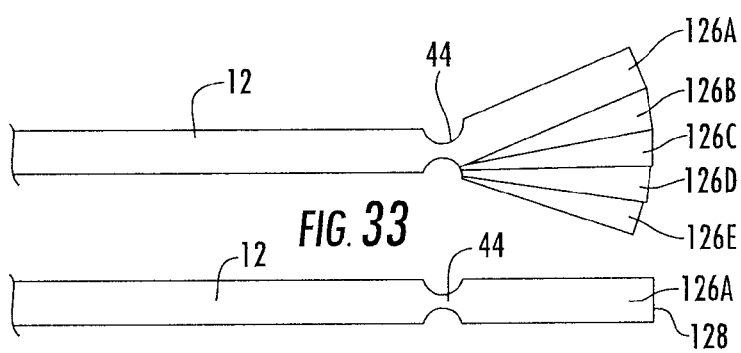
FIG. 33
FIG. 35
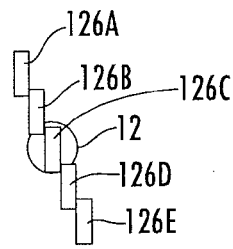
FIG. 34
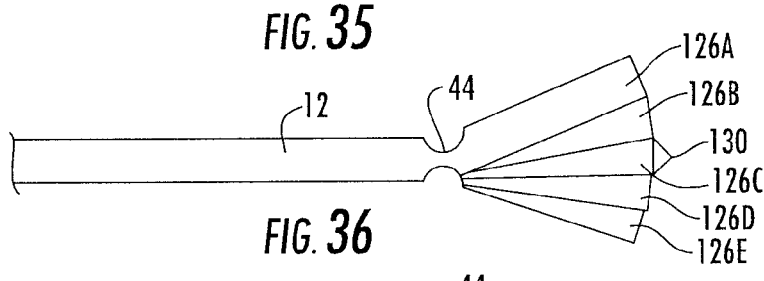
FIG. 36
FIG. 38
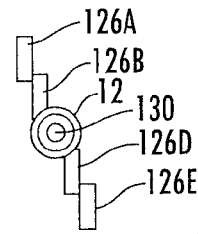
FIG. 37
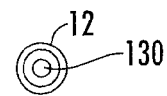
FIG. 39
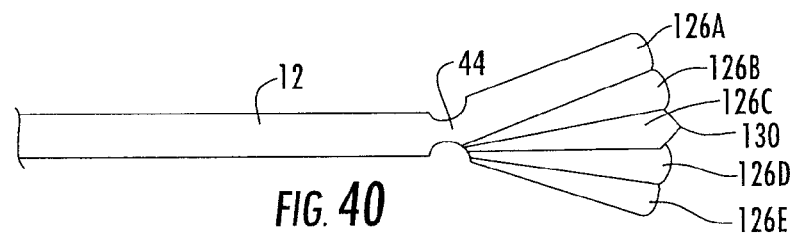
FIG. 40
FIG. 41
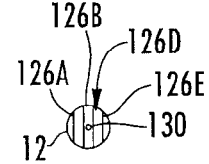
FIG. 42
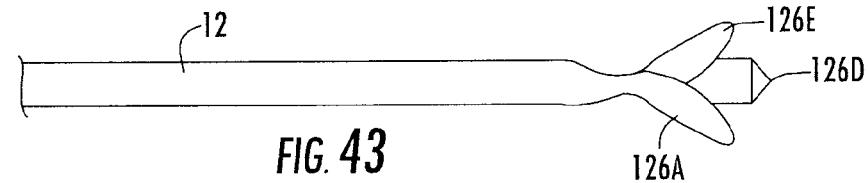
FIG. 43

VERTEBRAL CAVITATION SURGICAL TOOL

CROSS REFERENCE TO RELATED APPLICATIONS

This application claims priority under 35 USC 119(e) to the U.S. Provisional Application No. 61/454,022, filed on Mar. 18, 2011, entitled, "Vertebral Cavitation Surgical Tool", and U.S. Provisional Application No. 61/494,624, filed on Jun. 11, 2011, entitled, "Vertebral Cavitation Surgical Tool", the contents of which are herein incorporated by reference.

FIELD OF THE INVENTION

The invention relates to medical devices for creating cavities within body organs; and more particularly, to a device and system for creating cavities or voids in vertebral bodies.

BACKGROUND OF THE INVENTION

The central nervous system is a vital part of the human physiology that coordinates human activity. It is primarily made up of the brain and the spine. The spinal chord is made up of a bundle of nerve tissue which originates in the brain and branches out to various parts of the body, acting as a conduit to communicate neuronal signals from the brain to the rest of the body, including motor control and sensations. Protecting the spinal chord is the spinal, or vertebral, column. Anatomically, the spinal column is made up of several regions, including the cervical, thoracic, lumbar and sacral regions. The cervical spine is made up of seven vertebrae, and functions to support the weight of the head. The thoracic spine is made up of twelve vertebrae and functions to protect the organs located within the chest. Five vertebrae make up the lumber spine. The lumber spine contains the largest vertebra and functions as the main weight bearing portion of the spine. Located at the base of the spine is the five fused vertebrae known as the sacrum. The coccyx sits at the base of the spinal column and consists of four fused vertebrae.

Each of the vertebrae associated with the various spinal chord regions are made up of a vertebral body, a posterior arch, and transverse processes. The vertebral body, often described as having a drum-like shape, is designed to bear weight and withstand compression or loading. In between the vertebral bodies is the intervertebral disc. The intervertebral disc is filled with a soft, gelatinous-like substance which helps cushion the spine against various movements and can be the source of various diseases. The posterior arch of the vertebrae is made up of the lamina, pedicles and facet joints. Transverse processes extend outwardly from the vertebrae and provide the means for muscle and ligament attachment, which aid in movement and stabilization of the vertebra.

While most people have fully functional spinal chords, it is not uncommon for individuals to suffer some type of spinal ailment, including degenerative spine disease, spinal trauma, spinal tumors, or spinal chord/vertebral column abnormalities. Spinal fractures, or vertebra compression fractures, occur when one the bones of the spinal column fractures. Such an event is often accompanied by sudden onset of pain in the back which intensifies when sitting or standing and decreases when lying down. The pain associated with vertebra compression fractures can be strong enough to limit the activities a person can undertake, thereby reducing the overall quality of life of the individual. When the bone breaks, it often cracks and collapses, thereby becoming compressed. Typical bones in the skeleton system, such as long bones of the leg, which must be capable of handling rigorous movement, are more dense and rigid as compared to bones of the spinal system. The bones of the spinal chord, however, are less dense than other bones and contain spongy, soft bone areas, allowing the body to move in certain manners, such as bending and twisting. While these bones allow for such motions, they are more susceptible to fractures.

Vertebra compression fractures often result from physical injury or trauma. Various other conditions, such as osteoporosis and long term drug usage, including steroid usage, can make bones more fragile and therefore more prone to fractures. In addition, cancer, such as those that occur in the bone, i.e. multiple myeloma, and those that do not occur in the bone but metastasize and spread to the bone, i.e. breast or prostate cancer, weaken bone structure resulting in increased risk for vertebra compression fractures. Spinal fractures that are not properly treated can result in serious medical conditions, such as kyphosis (forward curvature of the spine) or dowager's hump. While the actual fracture may lessen in pain severity over time as the fracture heals, spinal fractures that are not treated, typically through surgical intervention, result in the bone healing in the fractured, collapsed position. A fracture that remains deformed, therefore, can shorten the spine and push it forward, thereby adversely affecting the alignment of the spine.

DESCRIPTION OF THE PRIOR ART

Numerous devices have been developed in an effort to treat spinal injuries. For example, U.S. Pat. No. 5,928,239 discloses a device and method for percutaneous surgical cavitation. The device includes an elongated shaft and cutting tip interconnected by a freely-rotating hinge. Upon rotation of the shaft to a sufficient velocity, the cutting tip will be deflected toward a position that is angularly offset from the shaft's access of rotation. The length of the cutting tip will determine the radius of the cavity being formed, which may be several times the radius of the shaft. The method of the present invention provides for formation of a cavity within a body through a small percutaneous access opening such that an enlarged cavity may be formed without an invasive access opening. The '239 patent also describes s a method of percutaneous prophylactic replacement of osteoporotic bone wherein weakened bone material is removed from a cavity using only a needle-sized access opening. Strengthening bone replacement material, such as bone cement, can be injected into the cavity to provide reinforcement of weakened bone without invasive surgical access.

U.S. Pat. No. 6,425,887 discloses a needle assembly including an infusion needle that includes a plurality of needle cannulae made of a superelastic material such as nitinol. The needle cannulae are cold-worked or heat annealed to produce preformed bends that can be straightened within passageway of a coaxial outer cannula for introduction into the body of a patient. Upon deployment from the outer cannula, the needle cannulae substantially return to their preformed configurations for the introduction or extraction of materials at areas lateral to the entry path of the needle assembly. The plurality of needle cannulae can be variably arranged or configured for their distal tip portions to attain a desired infusion pattern such as an umbrella shaped array, and/or be staggered axially.

U.S. Pat. No. 6,592,559 discloses a needle assembly including a needle that includes a needle cannula made of a superelastic material such as Nitinol. The needle cannula is cold-worked or heat annealed to produce a preformed bend that can be straightened within passageway of a coaxial outer cannula for introduction into the body of a patient. Upon deployment from the outer cannula, the needle cannula substantially returns to the preformed configuration for the introduction or extraction of materials at areas lateral to the entry path of the needle assembly. The needle assembly can comprise a plurality of needle cannulae that can be variably arranged or configured for attaining a desired infusion pattern.

U.S. Pat. No. 6,746,451 discloses a percutaneous surgical device and method for creating a cavity within tissue during a minimally invasive procedure. A cavitation device includes a shaft interconnected to a flexible cutting element. A flexible cutting element has a first shape suitable for minimally invasive passage into tissue. The flexible cutting element has a means to move toward a second shape suitable for forming a cavity in tissue. When used in bone, the resulting cavity is usually filled with bone cement or suitable bone replacement material that is injectable and hardens in situ. The disclosed cavitation device and methods can be used for the following applications: treatment or prevention of bone fracture, joint fusion, implant fixation, tissue harvesting (especially bone), removal of diseased tissue (hard or soft tissue), and general tissue removal.

U.S. Pat. No. 6,923,813 discloses several embodiments of cutting tips for tools for creating voids in interior body regions. The cutting tips provide for rotational and translational cutting. An actuator mechanism for deploying a cutting tip converts the rotational movement of a wheel into translational movement of a plunger rod. The actuator mechanism provides positive cutting action as the cutting tip is moved from a first, non-deployed position to a second, deployed position and from the second, deployed position to the first, non-deployed position. Methods of creating a void in bone provide one or more mechanical cutting tools that may be used in combination with one or more expandable void-creating structures to form a void of a desired size and configuration.

U.S. Publication No. 2007/0168041 discloses a method of replacing a nucleus pulposus in an intervertebral disc by filling the disc with a flowable augmentation material through a through bore in a pedicle. The device includes a tubular member constructed of a shape memory alloy that is used to create a throughbore from a pedicle of a first vertebra. Once in place, the distal end of the shape memory tube curves toward one of the end plates. The curved tube thereby creates a passage for the flexible drill and conduit for both disc tissue removal and augmentation material filling.

U.S. Publication No. 2009/0138043 discloses medical devices and methods for accessing a biological body. In one embodiment, a method includes inserting a cannula at least partially into a vertebra such that a threaded portion of the cannula secures the cannula to a portion of a cortical bone of the vertebra and forms a channel within the cortical bone. A medical device is inserted at least partially through the cannula such that a distal end portion of the medical device is disposed within a portion of a cancellous bone of the vertebra. A medical procedure is performed within the cancellous bone using the medical device and then the cannula and the medical device are removed from the vertebra, leaving a channel in the vertebra having at least partially threaded interior walls. A bone screw that has threads configured to matingly engage the threaded channel is then inserted into the threaded channel.

U.S. Publication No. 2010/0174267 discloses a needle assembly compromising an infusion needle that includes a needle cannula made of a superelastic material such as Nitinol. The needle cannula is cold-worked or heat annealed to produce a preformed bend that can be straightened within passageway of a coaxial outer cannula for introduction into the body of a patient. Upon deployment from the outer cannula, the needle cannula substantially returns to the preformed configuration for the introduction or extraction of materials at areas lateral to the entry path of the needle assembly. The needle assembly can compromise a plurality of needle cannulae that can be variably arranged or configured for attaining a desired infusion pattern.

U.S. Publication No. 2010/0185161 discloses a system and methods for channeling a path into bone. The system includes a trocar having a proximal end, distal end and a central channel disposed along a central axis of the trocar. The trocar includes a radial opening at or near the distal end of the trocar. The system includes a curveable cannula sized to be received in the central channel, the curveable cannula comprising a curveable distal end configured to be extended laterally outward from the radial opening in a curved path extending away from the trocar. The curveable cannula has a central passageway having a diameter configured to allow a probe to be delivered through the central passageway to a location beyond the curved path.

SUMMARY OF THE INVENTION

The instant invention describes a surgical tool for providing cavitations, or void spots, within the interior of body regions. The surgical tool is constructed and arranged to penetrate almost all interior body regions in which formation of a cavity or void space is necessary for diagnostic or treatment purposes. The surgical tool comprises an insertable member receiving structure sized and shaped to receive one or more insertable devices. The interior lumen of the insertable member receiving structure allows the insertable device to slide and/or rotate relative to the insertable member receiving structure and vice versa. At least one insertable member is a cavity forming device which has a plurality of cavity forming members constructed and arranged with spring-like characteristics for traversing between a cavity forming position and a non-cavity forming position. Upon traversal back to the cavity forming position, the displacement members retain their cavity-forming structural configurations.

Accordingly, it is an objective of the instant invention to teach an improved surgical tool for providing cavitations, or void spots, within the interior of the body regions.

It is a further objective of the instant invention to teach an improved surgical tool which can be used for providing cavitations in vertebral bodies.

It is yet another objective of the instant invention to teach an improved surgical tool which minimizes damage to vertebral body compact bone while forming cavities in soft, spongy bone.

It is a still further objective of the invention to teach an improved surgical device which minimizes the long-term affects associated with vertebral fractures.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 2 is an exploded view of the surgical tool with one or more insertable parts for providing cavitations within the interior of body regions in accordance with the instant invention;

FIG. 33 is an alternative embodiment of the cavity forming tip of the cavity forming device, which is illustrated in an open position;

FIG. 34 is a front view of the alternative embodiment of the cavity forming tip illustrated in FIG. 33;

FIG. 35 is a closed position view of the cavity forming tip of the cavity forming device illustrated in FIG. 33;

FIG. 36 is an alternative embodiment of the cavity forming tip of the cavity forming device, which is illustrated in an open position;

FIG. 37 is a front view of the alternative embodiment of the cavity forming tip illustrated in FIG. 36;

FIG. 38 is a closed position view of the cavity forming tip of the cavity forming device illustrated in FIG. 36;

FIG. 39 is a front view of the alternative embodiment of the cavity forming tip illustrated in FIG. 38;

FIG. 40 is an alternative embodiment of the cavity forming tip of the cavity forming device, which is illustrated in an open position;

FIG. 41 is a closed position view of the cavity forming tip of the cavity forming device illustrated in FIG. 40;

FIG. 42 is a front view of the alternative embodiment of the cavity forming tip illustrated in FIG. 41;

FIG. 43 is an open position view of the cavity forming tip of the cavity forming device illustrated in FIG. 41.

DETAILED DESCRIPTION OF THE INVENTION

Figure 1:
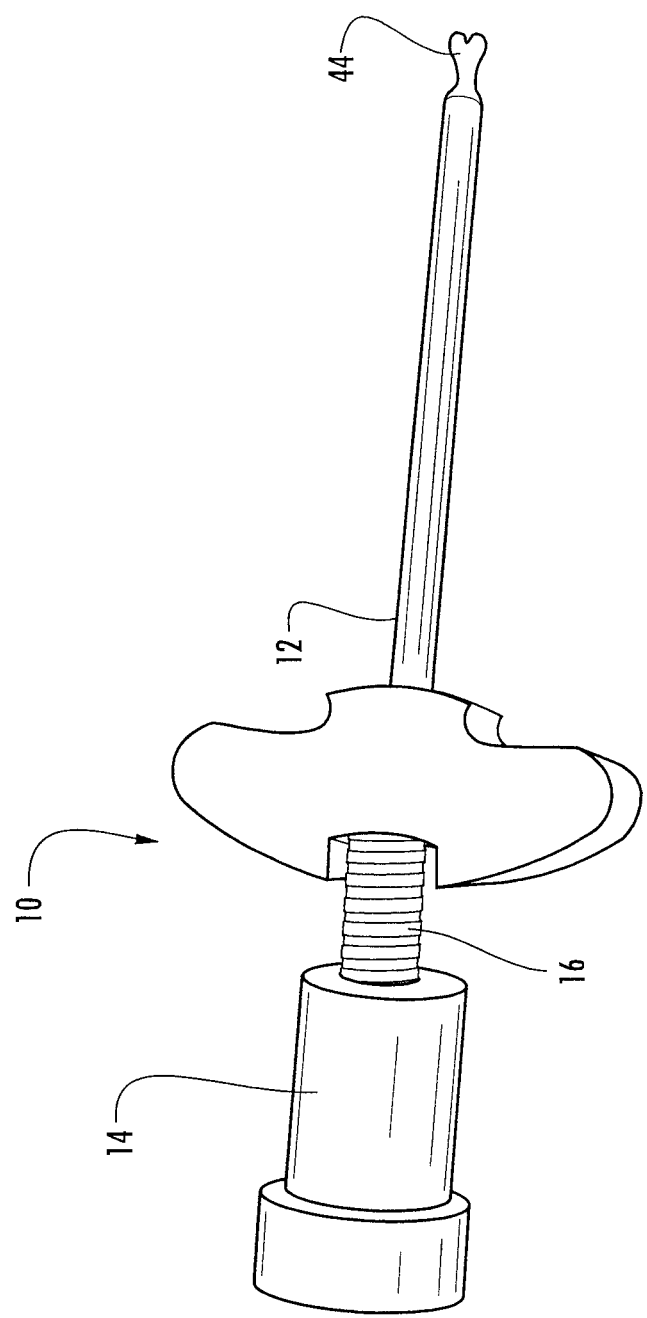
FIG. 1 is a perspective view of the surgical tool with one or more insertable parts for providing cavitations within the interior of body regions in accordance with the instant invention.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The instant invention describes a Jamshidi-style surgical tool with one or more insertable parts, illustrated generally as 10 (see FIG. 1), for providing cavitations, or void spots, within the interior of body regions, including tissues or organs. The surgical tool 10 is constructed and arranged to penetrate almost all interior body regions in which formation of a cavity or void space is necessary for diagnostic or treatment purposes. Referring to FIG. 2, an illustrative embodiment of the surgical tool 10 with one or more insertable parts is illustrated. The surgical tool 10 generally contains an insertable member receiving structure, such as a cannula, 12, one or more insertable devices, illustrated herein as a first insertable device 14, and a traversing member 16.

Figure 3A:
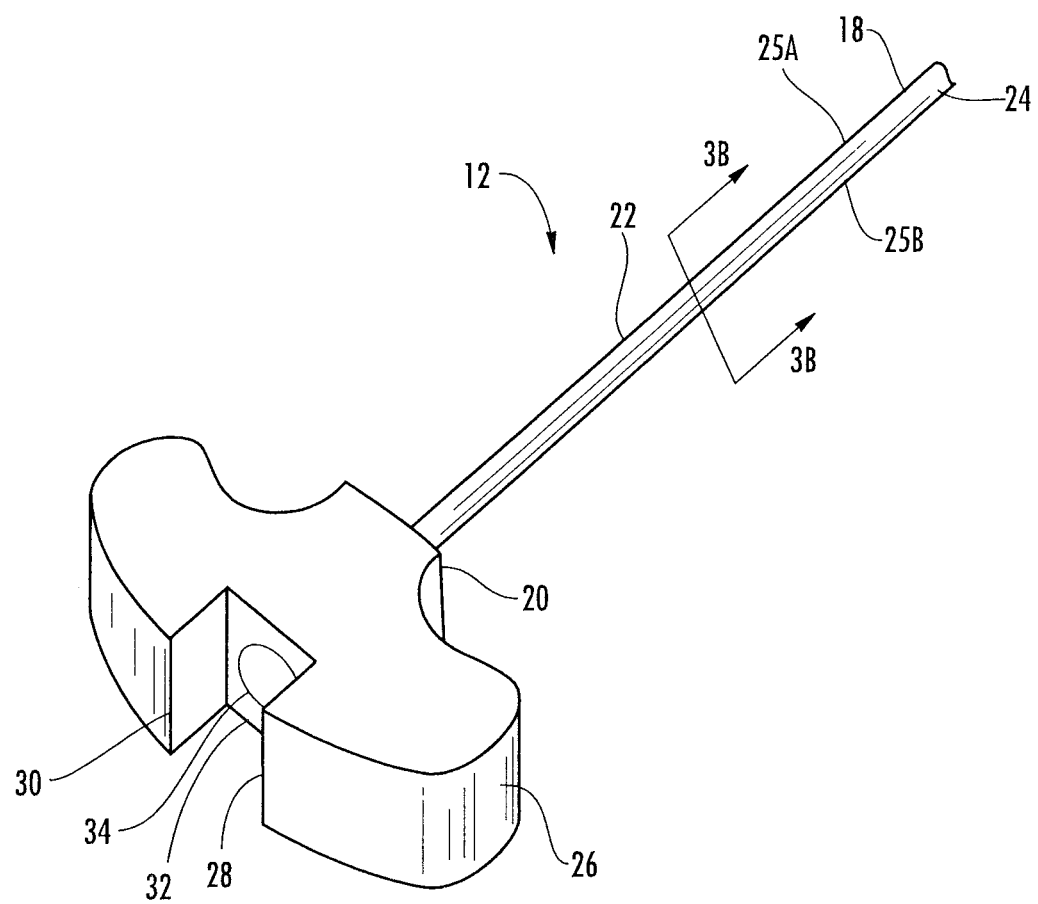
FIG. 3A is a perspective view of an illustrative example of the insertable member receiving structure.
Figure 3B:
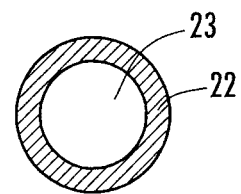
FIG. 3B is a cross-section view taken along 3B-3B of FIG. 3A.

Referring to FIG. 3A, the insertable member receiving structure 12 is illustrated as a generally tubular structure containing a distal end 18, a proximal end 20, and an insertable member receiving structure main body 22. The main body contains a longitudinal bore or inner lumen 23, see FIG. 3B, which is sized and shaped to allow one or more insertable devices to be inserted therein. The inner lumen 23 is also constructed and arranged to allow the insertable devices to move in a longitudinal direction, i.e. from the proximal end to the distal end, and to rotate within. The distal end 18 contains a tissue engaging tip 24. The tissue engaging tip 24 may be any shape, such as square shaped or rounded. Alternatively, the tissue engaging tip 24 may be a multi-faceted, triple crown cannulated tip. The insertable member receiving structure main body 22 may contain a pair of stabilizing wings 25A, 25B for stabilizing the device during rotation or for preventing the device from being inserted too deep into the bone. The proximal end 20 preferably contains a handle 26 for providing a user gripping and maneuvering ability. While the handle 26 is illustrated as a T-shaped handle, other handle configurations can be used as well. The handle 26 is ergonomically designed for comfortable use and can be made of any material known to one of skill in surgical tools art, such as rigid polymers or metals. The T-shaped handle 26 contains a cut out portion 28 which is sized and shaped to receive one or more insertable devices. Within the cut out area, insertable member receiving structure 12 contains an engaging member 30, illustrated herein as threading.

Fluidly coupled to the inner lumen 23 is a fluid delivering/aspirating member 32. The fluid delivering/aspirating member 32 contains an aperture 34 which is sized and shaped, and may be flared, to allow the insertable devices to be inserted therein and enter the inner lumen 23. Additionally, the fluid delivering/aspirating member 32 may be sized, shaped, and adapted to attach to the distal portion of a syringe. Accordingly, the fluid delivering/aspirating member 32 may contain male/female threading corresponding to the female/male threading of a syringe or snap-fit type fasteners. Preferably, the fluid delivering/aspirating member 32 is constructed as one portion of a luer lock system, such as a luer lock tip or luer slip tip of luer locking syringes, or other male/female luer adapters, known to one of skill in the art, and is sized and shaped to receive the corresponding member of the luer lock system. In this manner, fluids, such as bone cement or bone growth compositions, may be inserted into the lumen and dispensed to the cavity or void space, or aspirated from the cavity to the syringe.

Figure 4:
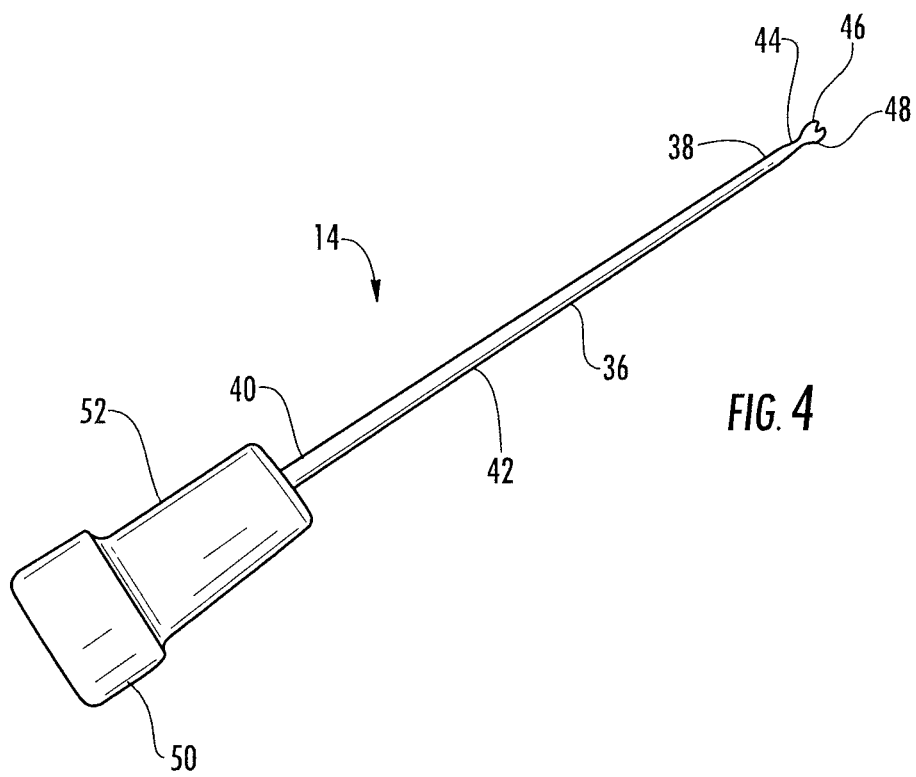
FIG. 4 is a perspective view of an illustrative example of an insertable device, illustrated as a cavity forming device.

Referring to FIG. 4, a first insertable device 14 is shown. The first insertable device 14 is illustrated as a cavity forming device 36, comprising a distal end 38, a proximal end 40, and a cavity forming device main body 42 traversing between the distal end 38 and the proximal end 40. The distal end 38 contains a cavity forming tip 44 which is preferably coupled to the cavity forming device main body 42 as a single unitary piece. In this manner, the cavity forming device main body 42 and the cavity forming tip 44 is made of the same material. Alternatively, the cavity forming tip can be made as a separate unit and subsequently attached to the cavity forming device main body 42. The cavity forming tip 44 is preferably made of independent displacement members 46 and 48, which when inserted into a tissue and rotated, act in unison to provide a cavity. While the cavity forming tip 44 may be adapted for use in any body region, it is preferably adapted for use in vertebral bodies. The unique aspect of the instant invention is that the cavity forming tip 44 and displacement members 46 and 48, are designed to easily form cavities within the cancellous (soft, sponge-like portion) while not damaging any compact bone which comes in contact with the cavity forming tip 44. In this manner, the user can be assured that a cavity is formed in the desired place without the increased risk of damaging the harder, external portions, thereby causing unintended medical problems.

Figure 5A:
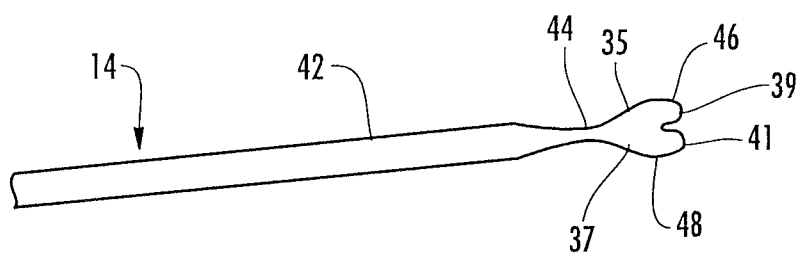
FIG. 5A is a partial perspective view of the cavity forming device, illustrating the cavity forming tip.
Figure 17:
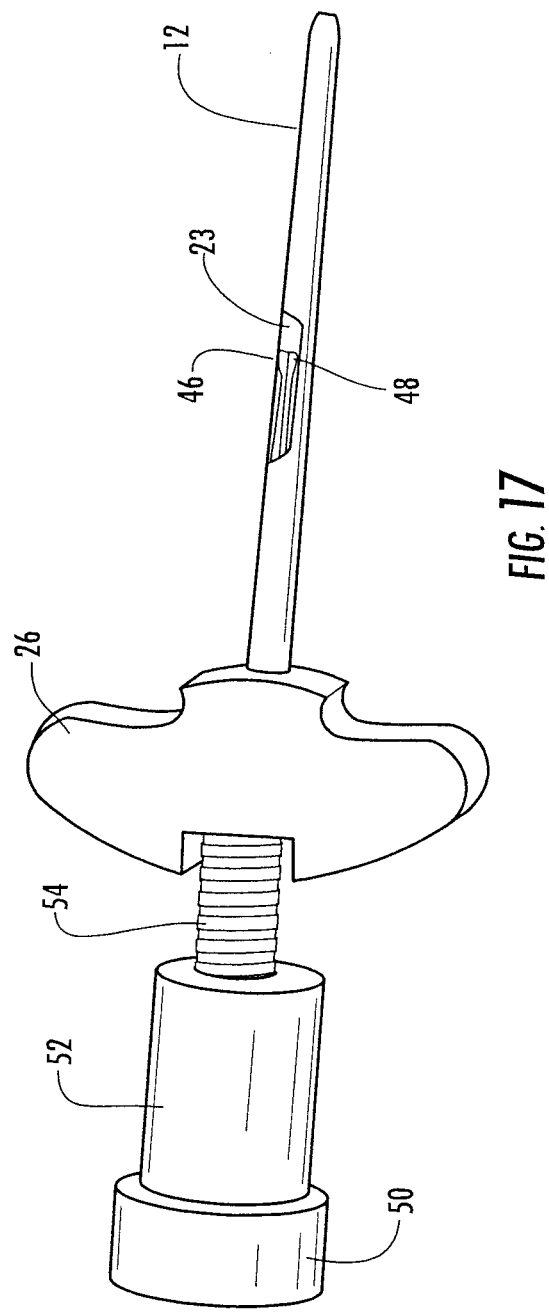
FIG. 17 illustrates the cavity forming device inserted within the insertable member receiving structure, showing partial cut out of the cavity forming members in a non-cavity forming position.

FIG. 5A illustrates a partial perspective view of an illustrative example of the first insertable device 14, illustrating the cavity forming tip 44. The displacement members 46 and 48 can be sized and shaped according to the size and shape of the cavity desired. For example, the displacement members 46 and 48 illustrated in FIG. 5A contain curved portions 35 and 37 with generally rounded terminal ends 39 and 41. Each of the displacement members 46 and 48 are adapted to traverse from a first position to a second position. Preferably, the displacement members 46 and 48 are made of a material that has spring-like action, traversing between multiple positions. In this manner, the spring-like action allows the displacement members 46 and 48 to move relative to each other when a predetermined force is applied and assume the their original position when the force is removed. Preferably, the displacement members are made of nickel titanium (Nitinol, NiTi). Alternatively, they can be made of other superelastic alloys which can be constrained into a first shape and then deployed to a second shape without experiencing plastic deformity. As illustrated, the displacement members 46 and 48 are shown in the cavity forming position. In this position, they are arranged in an overlap alignment in which displacement member 46 rests partially on top of displacement member 48, similar to the arrangement of scissors when in the open position. Since each of the displacement members has spring-like properties, upon contact with a surface having certain hardness or resistance, the displacement member 46 and/or 48 traverse to a second non-cavity forming position. In this position, the displacement member 46 is in a parallel arrangement with and resting above or on top of the displacement member 48, see for example, FIG. 17. In an alternative embodiment, a spring mechanism may be used to provide traversal between the two positions.

Figure 5B:
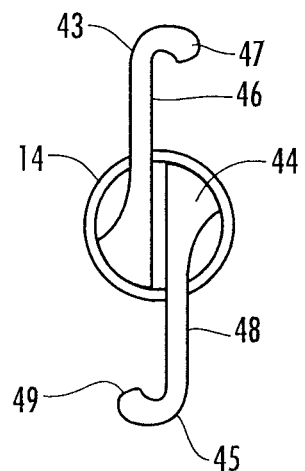
FIG. 5B is a front view of an alternative embodiment of the cavity forming tip of the cavity forming device.
Figure 5C:
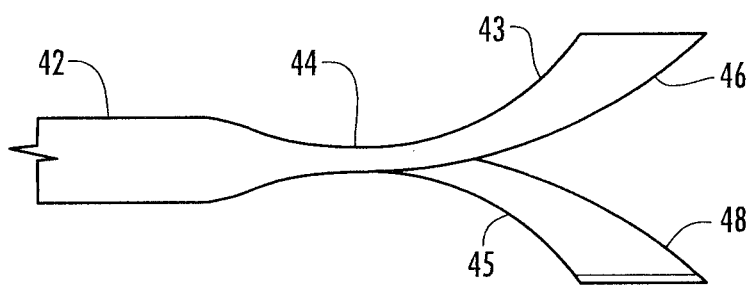
FIG. 5C is a side view of the alternative embodiment of the cavity forming tip of the cavity forming device illustrated in FIG. 5B.
Figure 5D:
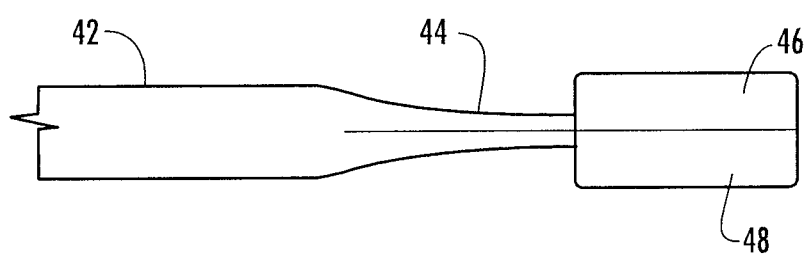
FIG. 5D is a top view of the alternative embodiment of the cavity forming tip of the cavity forming device illustrated in FIG. 5B.
Figure 5E:
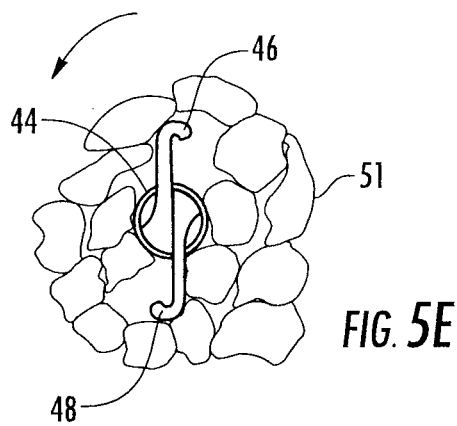
FIG. 5E illustrates the first position of the displacing members inserted within a vertebral bone prior to rotation.
Figure 5F:
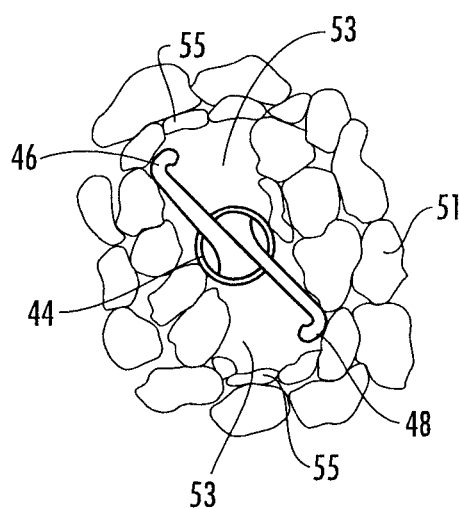
FIG. 5F illustrates rotation of the displacing members inserted within a vertebral bone, thereby forming a cavity.
Figure 5G:
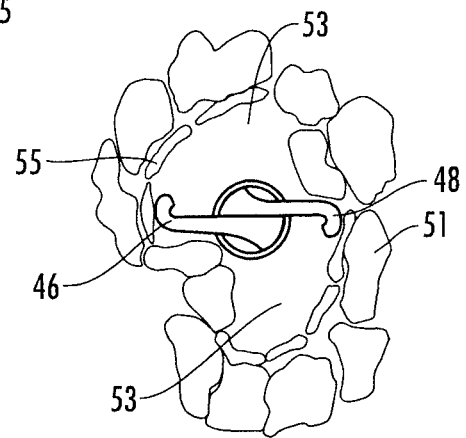
FIG. 5G illustrates the displacing members being rotated about 90 degrees from their original position.

Referring to FIGS. 5B-5D, an alternative embodiment of the cavity forming tip 44 is illustrated. The cavity forming tip 44 contains displacement members 46 and 48, each having similar characteristics as described above. Each of the displacement members 46 and 48 have curved portions 43 and 45 respectively, forming hook or semi-hooked terminal ends 47 and 49. While the terminal ends 47 and 49 are illustrated generally as being separated by 180 degrees, such arrangement is illustrative only. In any embodiment, the displacing members 46 and 48 function to displace cells, cellular debris, or tissue components from a body organ/tissue to form a void or cavity therein. The displacement members 46 and 48 illustrated in FIGS. 5B-5D are shown forming a cavity within the soft bone area of a vertebral body in FIGS. 5E-5G. Referring specifically to FIG. 5E, the cavity forming tip 44 is shown in a first position inserted within the cancellous bone 51 of the vertebral body. As the cavity forming tip 44 is rotated, the displacing members 46 and 48 rotate as well. The displacing members 46 and 48 contact the cancellous bone 51 as they rotate, displacing the cancellous bone from its original position to a second position, see FIG. 5F. The displacement of the bone from the first position to the second position forms a cavity 53. Some of the cancellous bone 51 displaced by the displacing members may become compacted 55. FIG. 5G illustrates the displacing members 46 and 48 rotated about 90 degrees from their original position, thereby forming a larger portion of the cavity 53.

Figure 6:
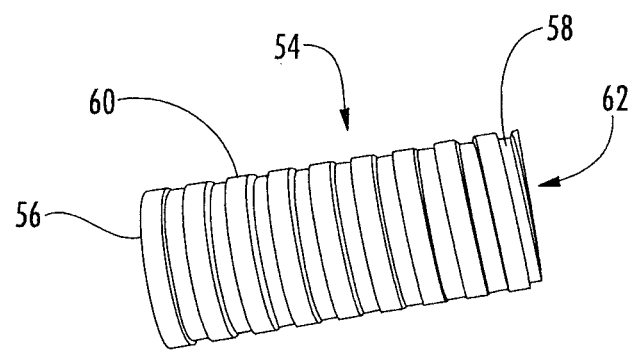
FIG. 6 is a perspective view of the traversing sleeve.

Referring back to FIG. 4, the proximal end 40 contains a rotating member, illustrated as a knob 50, for providing the user the ability to place the cavity forming device 36 into the outer sleeve member 12 and/or for rotation of the cavity forming device 36. The rotating member further contains a traversing sleeve receiving member 52 constructed and arranged to couple and rotatably engage with a traversing sleeve 54. Referring to FIG. 6, the traversing sleeve 54 is illustrated in a generally cylindrical shape having a first end 56 and a second end 58. This shape, however, is not a limiting shape as other shapes may be employed. The outer surface 60 of the traversing sleeve 54 is threaded in a manner which couples to internal threading (not illustrated) of the traversing sleeve receiving member 52. A lumen 62 is sized and shaped to provide passage of the cavity forming device main body 42. Additionally, the traversing sleeve 54 contains an inner surface (not illustrated) having internal threading (not illustrated) at or near the second end. The internal threading is designed to engage the threading of the engaging member 30 of the insertable member receiving structure 12. The first end 56 of the traversing sleeve 54 is secured to the traversing sleeve receiving member 52 and the second end 58 of the traversing sleeve 54 is secured to the insertable member receiving structure 12. As the user turns the knob 50, the traversing sleeve receiving member 52 screws into the traversing sleeve 54, providing the cavity forming device 36 linear motion toward the distal end of the insertable member receiving structure 12. As the knob 50 moves linearly from the proximal end toward the distal end, the displacement members rotate, thereby providing cavity forming function.

Figure 7:
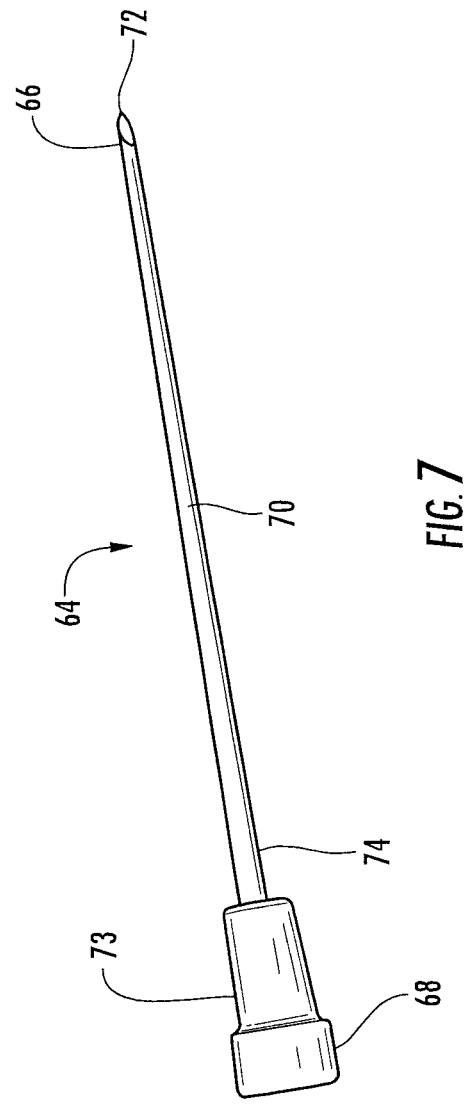
FIG. 7 is a perspective view of an illustrative example of a second insertable device, illustrated as a trocar.
Figure 8A:
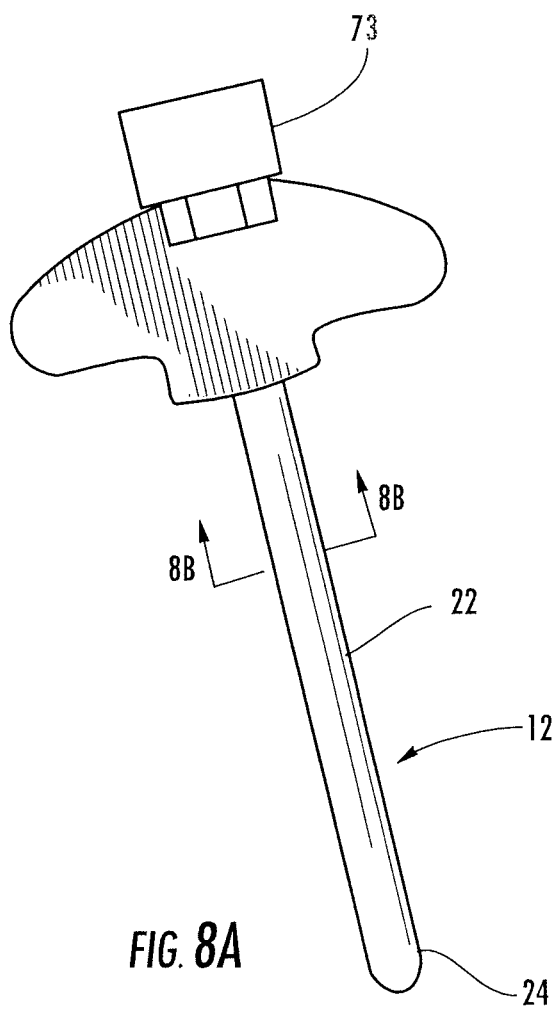
FIG. 8A is a perspective view of the trocar inserted into the insertable member receiving structure.
Figure 8B:
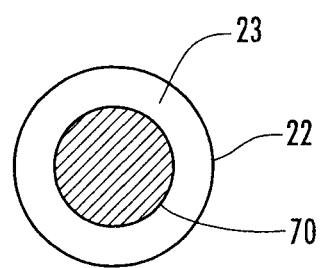
FIG. 8B is a cross sectional view of the surgical tool illustrated in FIG. 8A, taken along lines 8B-8B.

FIG. 7 illustrates a second insertable device, illustrated herein as a trocar 64. The trocar 64 has a distal end 66, a proximal end 68, and a main body 70 traversing between the distal end and the proximal end. The distal end 66 contains a sharp pointed end 72, preferably three sided, for insertion into a hard surface. The main body 70 is sized and shaped to be insertable within the lumen 23 of the insertable member receiving structure 12, see FIGS. 8A and 8B. The proximal end 68 contains a handle 73 for aiding the user when inserting within the insertable member receiving structure 12. The handle 73 may contain threading (not illustrated) along the internal surface 74 which is constructed and arranged to engage with the threading 30 of the insertable member receiving structure 12.

Figure 9:
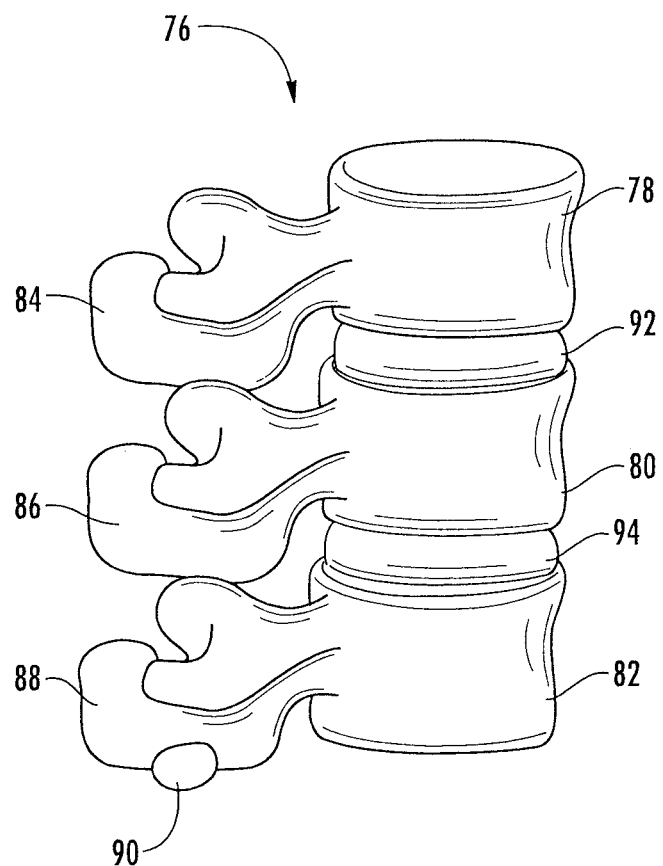
FIG. 9 is a perspective view of a portion of a healthy spine.
Figure 10:
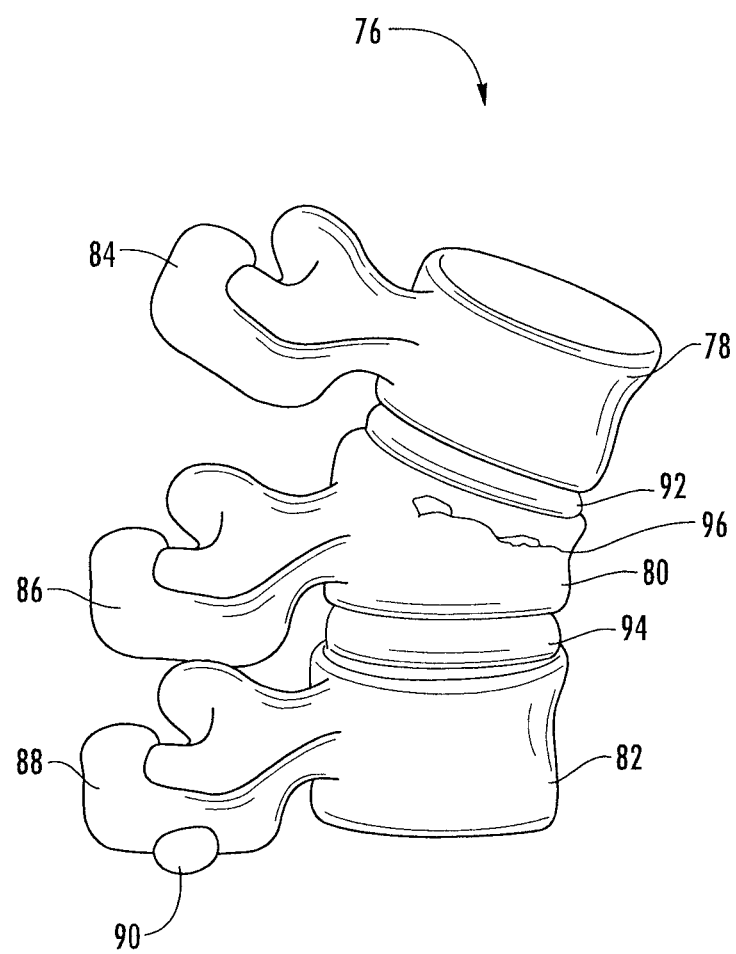
FIG. 10 is a perspective view of the spine illustrated in FIG. 9 with a vertebra compression fracture.
Figure 11:
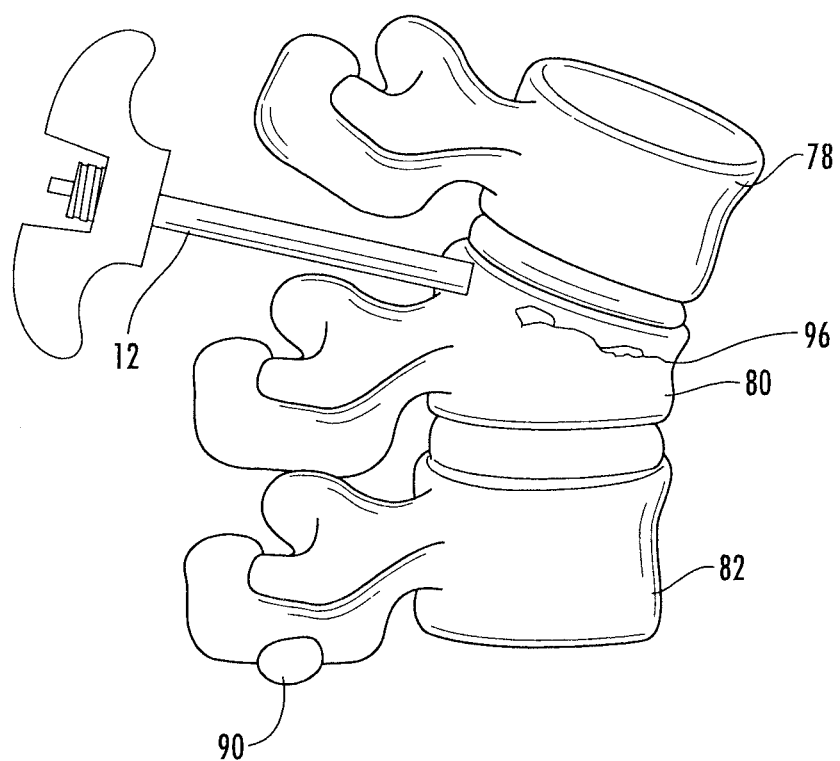
FIG. 11 illustrates insertion of the insertable member receiving structure into the vertebral body having a vertebra compression fracture.
Figure 12:
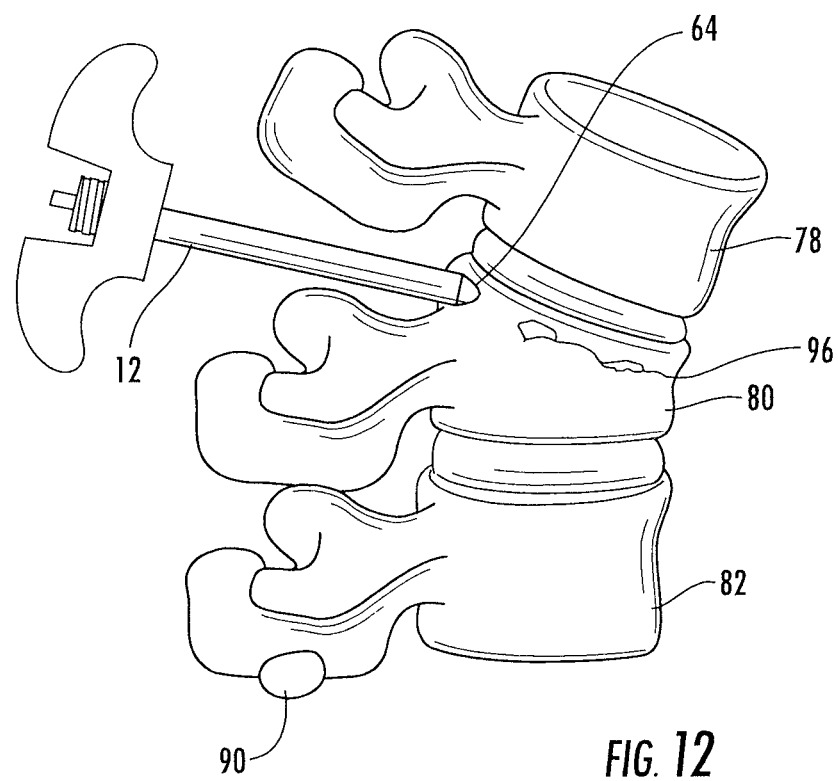
FIG. 12 illustrates insertion of the insertable member receiving structure with a trocar inserted therein.
Figure 13:
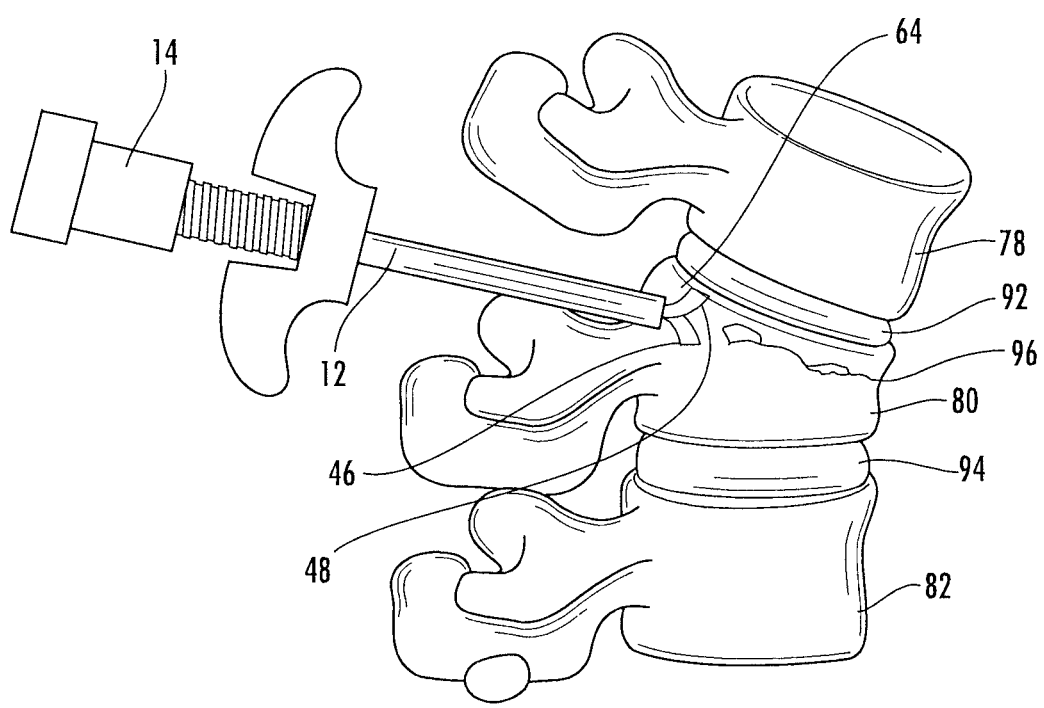
FIG. 13 illustrates insertion of the cavity forming device within the insertable member receiving structure.
Figure 14:
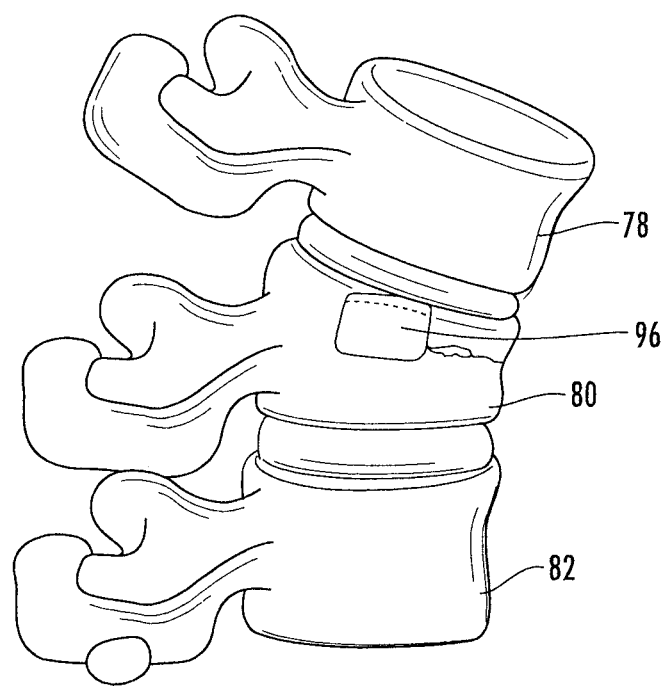
FIG. 14 illustrates the formation of a cavity within the vertebral body.
Figure 15:
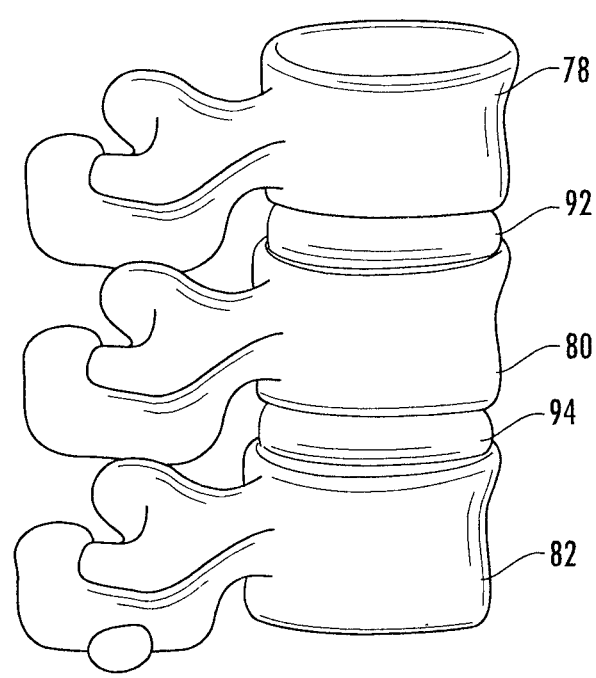
FIG. 15 illustrates the spine shown in FIG. 10 restored to, or near its pre-vertebra compression fracture anatomical shape.

FIGS. 9-15 illustrate the features of the surgical tool 10 when used in a vertebral surgical procedure, such as treatment of a fractured spinal vertebra. FIG. 9 illustrates a portion of a healthy spine 76 having vertebral bodies 78, 80, 82, with spinous process 84, 86, and 88 respectively, and facet joint illustrated at 90. Each of the vertebral bodies is separated by intervertebral discs, 92 and 94. FIG. 10 illustrates the spine 76 shown in FIG. 9 having a vertebra compression fracture 96 in vertebral body 80. The vertebra compression fracture 96 causes the vertebral body 80 to collapse, resulting in movement and misalignment of vertebral body 78. In order to prevent complications associated with vertebra compression fractures, the patient typically undergoes a surgical procedure in which the surgeon inserts (using techniques known to surgeons performing spinal surgeries) the surgical tool 10 into the patient's spine at the damaged vertebral body. The insertable member receiving structure 12 of the surgical tool 10 contacts the vertebral body 80 (FIG. 11). With the aid of the trocar 64 inserted within and secured to the insertable member receiving structure 12, the surgical tool 10 is inserted into the vertebral body to a location at or near the vertebra compression fracture 96 (see FIG. 12). Once the surgical tool 10 reaches the desired place and is ready for formation of a cavity, the trocar 64 is removed from the insertable member receiving structure and replaced with the cavity forming device 36, see FIG. 13, to form a cavity 102, see FIG. 14, and restore the vertebral body 80 back to its original, or near original, shape, see FIG. 15.

Figure 16:
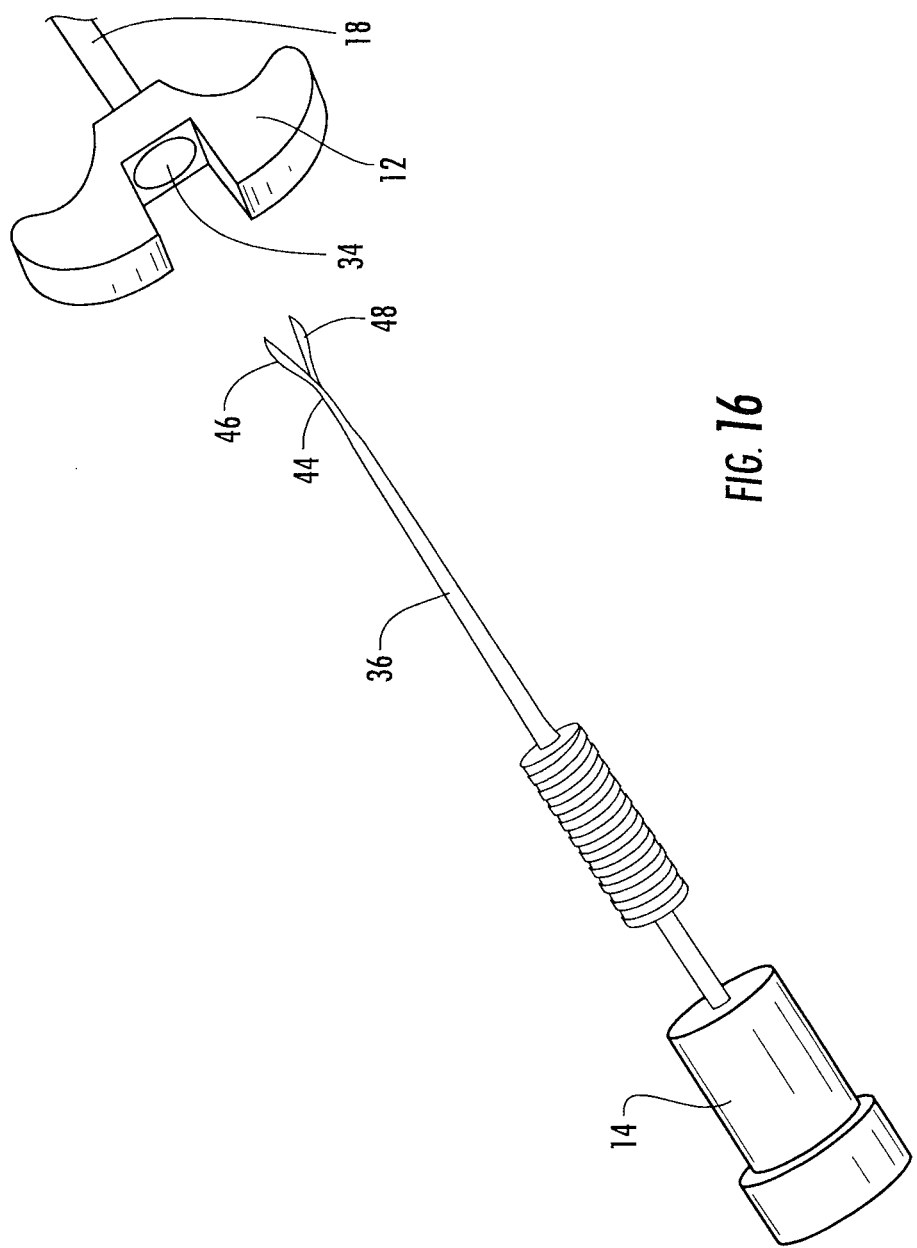
FIG. 16 illustrates the cavity forming device of the surgical tool in accordance with the instant invention prior to insertion into the insertable member receiving structure, showing the cavity forming members in the cavity-forming position.

Referring to FIG. 16, the cavity forming device 36 is illustrated prior to insertion into the inner lumen 23 of the insertable member receiving structure 12. Insertion is done by sliding the cavity forming tip 44 into the aperture 34 and moving the cavity forming device 36 towards the distal end 18 of the outer insertable member receiving structure 12. As the cavity forming tip 44 is inserted into the aperture 34, the spring-like nature of the displacement members 46 and 48 allows them to traverse from a cavity forming position, in which the plane of one displacement member diverges from the plane of the other displacement member, to a non-cavity forming position. In the non-cavity forming position, each displacement member 46 and 48 is arranged in a parallel fashion in which one displacement member rest on top of the other, i.e. they have converging planes, see FIG. 17. The cavity forming tip 44 may be designed such that should one displacement member retract to the non-cavity forming position, the other displacement member retracts as well. Alternatively, the cavity forming tip 44 may be constructed such that should one displacement member retract to the non-cavity forming position, the other displacement member remains in the cavity forming position. The first end 56 of the traversing sleeve 54 may then be secured to the traversing sleeve receiving member 52 as described above. Once secured, the second end 58 of the traversing sleeve 54 is secured to the engaging member 30 of the insertable member receiving structure 12 as described previously. Alternatively, the surgeon may first attach the second end 58 of the traversing sleeve 54 to the engaging member 30 prior to attaching the first end to the traversing sleeve receiving member 52.

Figure 18:
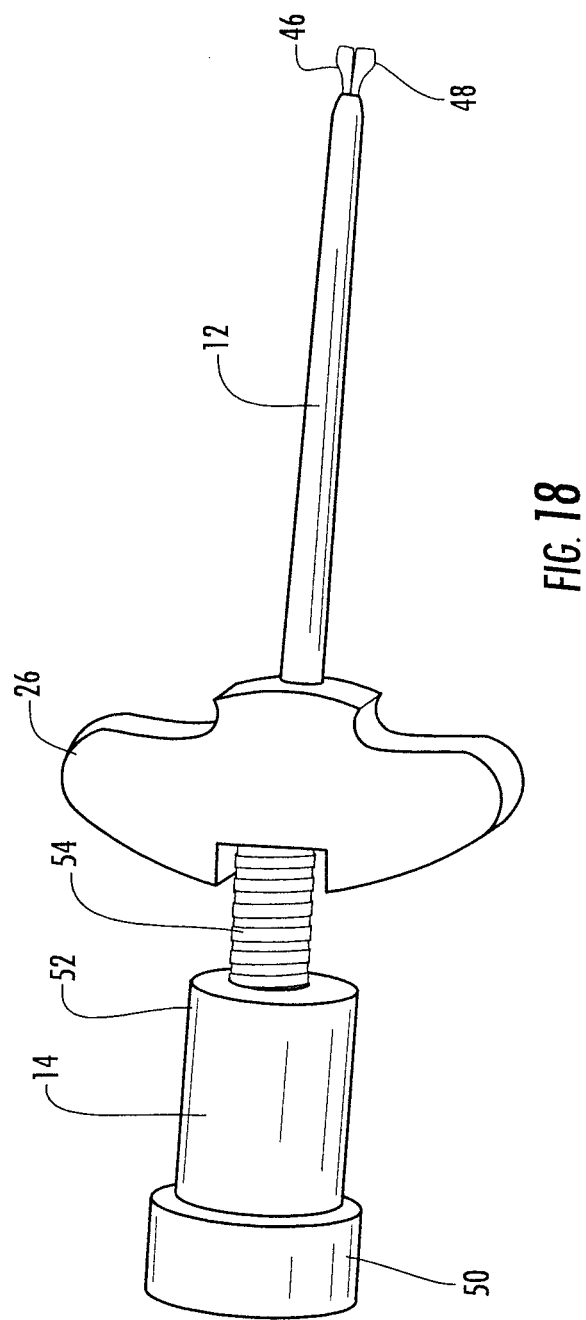
FIG. 18 illustrates the cavity forming device inserted within the insertable member receiving structure, showing the cavity forming members inserted through the insertable member receiving structure and illustrating the cavity forming members in the cavity forming position.

Once the cavity forming tip 44 traverses the length of the lumen 23 and exits out, the spring-like characteristics allow the displacement members 46 and 48 to traverse back to the cavity forming position, see FIG. 18. The degree of separation between the displacement members 46 and 48 can be controlled by limiting how far the cavity forming tip 44 travels through the lumen 23. Once located at the correct position, the user rotates the knob 50. Rotation of knob 50 causes the cavity forming device 36 to move in a linear direction towards the distal end of the insertable member receiving structure 12 as the traversing sleeve receiving member 52 rotatably engages the traversing sleeve. As the knob 50 gets rotated, the displacement members 46 and 48 move as well, forming a cavity as they undergo rotational movement.

Figure 19:
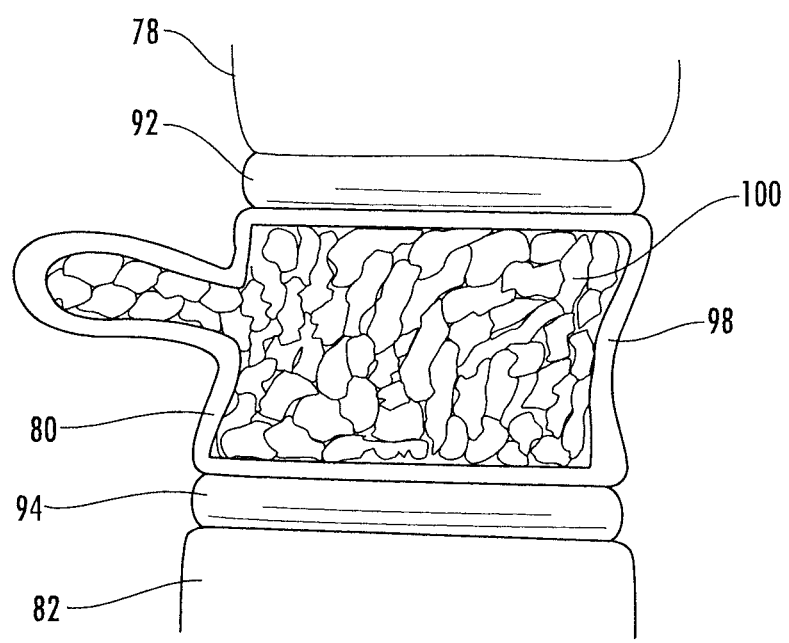
FIG. 19 is a cross sectional view of a vertebral body.
Figure 20:
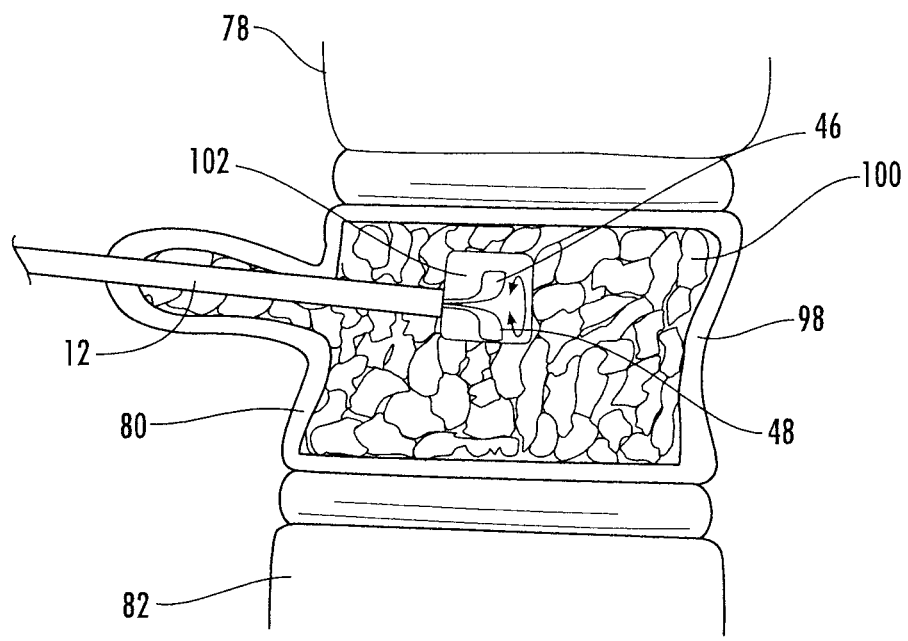
FIG. 20 is a cross sectional view of the vertebral body illustrated in FIG. 19 having the cavity forming device in accordance with the instant invention inserted therein.
Figure 21:
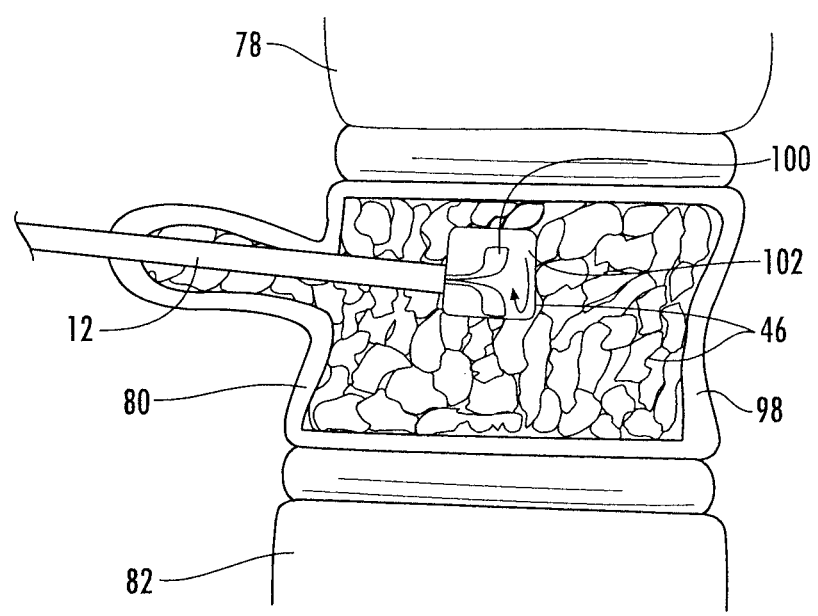
FIG. 21 is a cross sectional view of the vertebral body illustrated in FIG. 20, illustrating the rotation of the cavity forming device.
Figure 22:
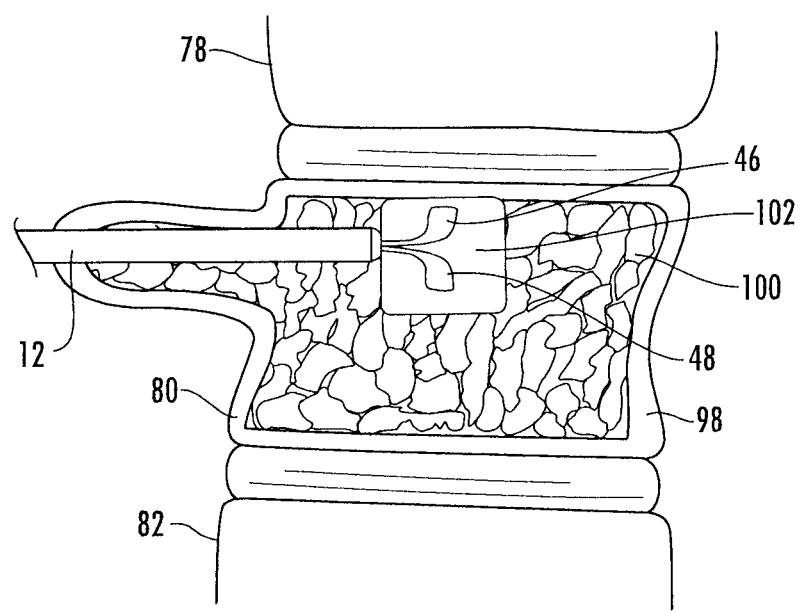
FIG. 22 is a cross sectional view of the vertebral body illustrated in FIG. 21 showing the cavity forming members contacting the compact bone of the vertebral body.
Figure 23:
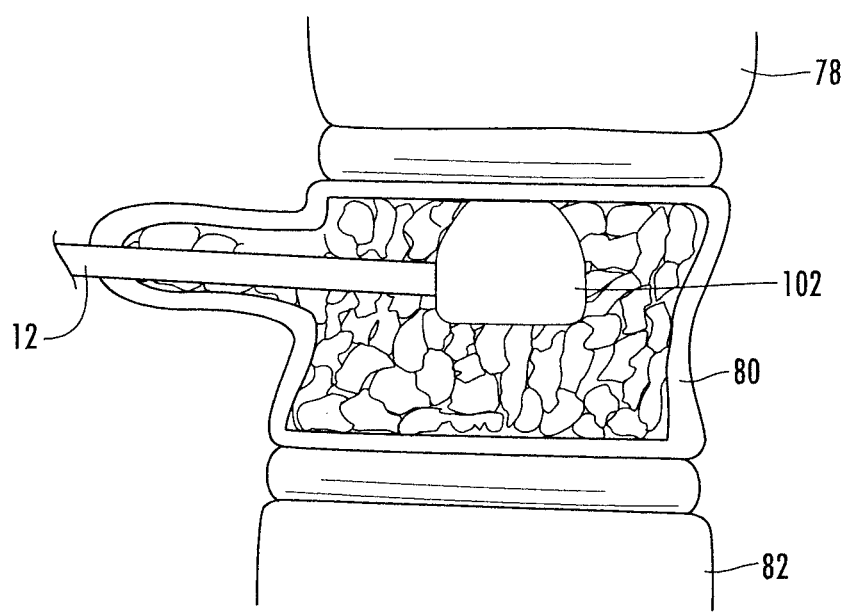
FIG. 23 is a cross sectional view of the vertebral body illustrated in FIG. 22 showing the formation of a cavity.

FIGS. 19-23 illustrate the formation of a cavity within the vertebral body 80. FIG. 19 is a cross sectional view of the vertebral body 80 showing compact bone 98 and cancellous, (soft, sponge) bone 100. Once the cavity forming device 36, with the displacement members 46 and 48 in the cavity forming position, is inserted into the vertebral body 80 and rotates, see FIGS. 20 and 21, a cavity, or void space, 102 is formed. As the cavity 102 is expanded, should either of the displacement members 46 or 48 contact any portion of the compact bone 98, they traverse from the cavity forming position to the non-cavity forming position, thereby preventing the compact bone from being damaged. Where the displacement member contacts the bone, there is no cavity formation, see FIGS. 22-23. Once the displacement member moves away from the compact bone, the member springs back to the cavity forming position.

Figure 24:
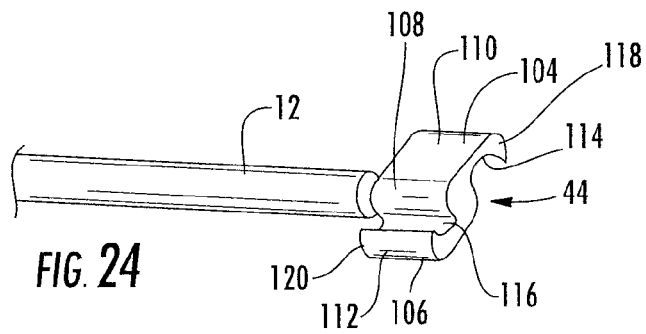
FIG. 24 is a perspective view of an alternative embodiment of the cavity forming tip of the cavity forming device.
Figure 25:
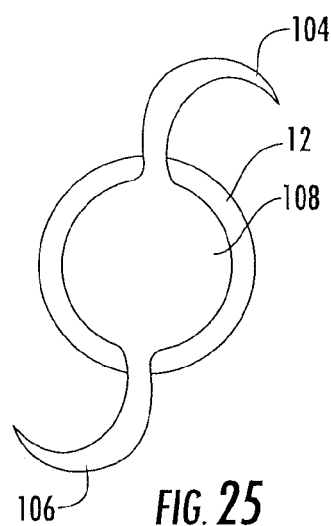
FIG. 25 is a front view of the alternative embodiment of the cavity forming tip illustrated in FIG. 24.
Figure 26:
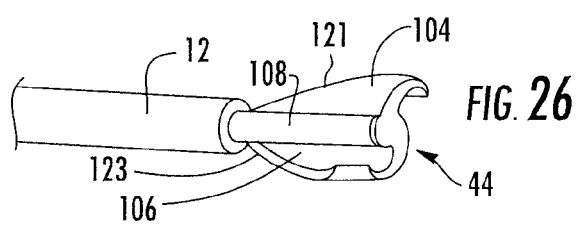
FIG. 26 is a perspective view of an alternative embodiment of the cavity forming tip of the cavity forming device.
Figure 27:
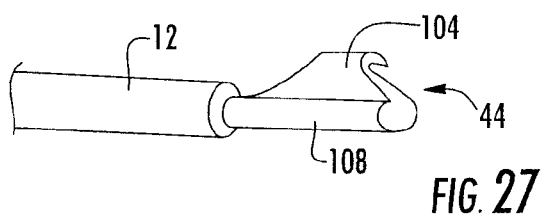
FIG. 27 is a perspective view of the alternative embodiment of the cavity forming tip illustrated in FIG. 24 or 26, illustrating use of a single displacement member.
Figure 28:
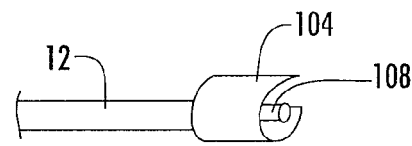
FIG. 28 is a perspective view of the alternative embodiment of the cavity forming tip illustrated in FIG. 24, illustrating the first displacement member expanding to the cavity forming position.
Figure 29:
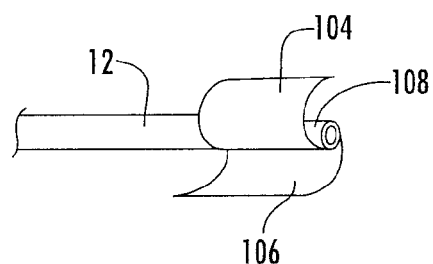
FIG. 29 is a perspective view of the alternative embodiment of the cavity forming tip illustrated in FIG. 24, illustrating the second displacement member expanding to the cavity forming position.

FIGS. 24-29 illustrate alternative embodiments of the cavity forming tip 44. Referring specifically to FIG. 24, the cavity forming tip 44 is shown extending from the insertable member receiving structure 12. The cavity forming tip 44 contains a first displacement member 104 and a second displacement member 106 arranged around a center member 108. Both displacement members 104 and 106 comprise a first surface 110 and 112 respectively, and a second surface 114 and 116, respectively. The first surfaces 110 and 112 contain curved portions 118 and 120 which provide a generally S-shaped configuration in cross section or when viewed from the front end (FIG. 25). The first and second displacement members 104 and 106 are arranged to allow for each of the surfaces 104 and 106 to contact the bone material as the tip 44 rotates, thereby compressing the bone material as it rotates. The displacement members 104 and 106 have the same spring-like nature as described for displacement members 46 and 48 which allows them to traverse between a cavity forming position and a non-cavity forming position. FIG. 26 illustrates an alternative embodiment of the displacement tip illustrated in FIG. 24. The cavity forming tip 44 illustrated in FIG. 26 comprises displacement members 104 and 106 which have edge 121 and 123 which are angled to form a V-shape and the generally S-shaped cross section is not maintained throughout. While the tip 44 is shown with displacement members 104 and 106, an alternative embodiment may include a single displacement member 104 or 106, see FIG. 27. In the non-cavity forming position, each of the members 104 and 106 can be configured around the center member 108. This position is typically used when inserting the cavity forming tip 44 into the insertable member receiving structure 12, allowing the tip 44 to traverse the length of the insertable member receiving structure without expanding. As soon as the tip 44 reaches the distal end, the first displacement member 104 unwinds. At a certain point, the second displacement member 106 unwinds until both members expand to the cavity forming position, see FIGS. 28 and 29. Alternatively, each displacement member 104 and 106 can be designed to expand into the cavity forming position instantaneously.

Figure 30:
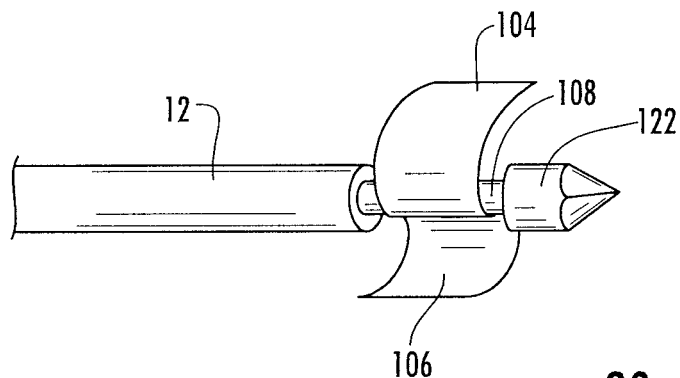
FIG. 30 is an alternative embodiment of the cavity forming tip of the cavity forming device.
Figure 31:
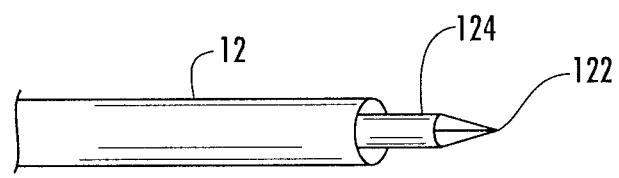
FIG. 31 is a perspective view of an alternative embodiment of the cavity forming tip of the cavity forming device, illustrated in a first non-cavity forming position.
Figure 32:
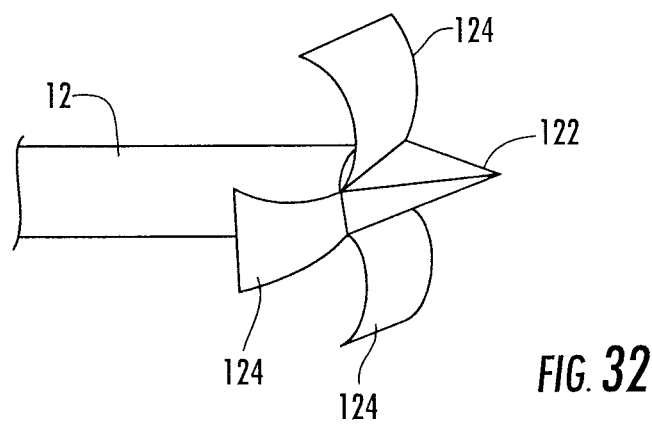
FIG. 32 is a perspective view of the alternative embodiment of the cavity forming tip illustrated in FIG. 31, shown in a cavity forming position.

Referring to FIGS. 30-32, the cavity forming tip 44 illustrated in FIGS. 24-26 is shown with a tip member 122 arranged on the distal end of the center member 108. In this configuration, the displacement members 104 and 106, when in the cavity forming position, are positioned between the tip member 122 and the distal end of the insertable member receiving structure 12. The tip member 122 may include, but is not limited to, a trocar tip, a beveled tip, a pencil tip, a blunt tip, a screw tip, or a drill tip. Referring to FIGS. 31-32, the tip member 122 may be designed such that as the tip member 122 contacts a surface or object at a pre-determined force, the tip member 122 retracts in an inwardly direction, i.e. toward the insertable member receiving structure 12. A displacement member 124 is coupled to the cavity forming tip 44 and is arranged in such a manner, that in the non-cavity forming position, it can traverse the length of the insertable member receiving structure 12 without expanding or unwinding. As illustrated in FIG. 31, the displacement member 124 is shown in the non-cavity forming position and is wrapped around a portion of the displacement tip, such as the center member 108, and/or a portion of tip member 122. As the tip member 122 pushes against a surface, displacement member 124 expands into a cavity forming position.

FIGS. 33-35 illustrate an alternative embodiment of the cavity forming tip 44, illustrated herein as a plurality of individually formed displacement members 126A-126E, collectively referred to as 126. The displacement members 126 may be formed as single unit, such as a nitinol wire, that is split and shaped into a desired configuration. Alternatively, the displacement members 126 may be formed as individual components and coupled together. The displacement members 126 have the same spring-like nature as described for displacement members 46 and 48, which allows them to traverse from a cavity forming position (fan-like configuration, open position) to a non-cavity forming position (closed position), see FIG. 35, in which each of the individually formed displacement members align to form a single member. Preferably, each of the displacement members 126A-126E are the same, or similarly, sized so that in the closed position, all the displacement members align forming an edge 128 that is generally linear.

FIGS. 36-39 illustrate an alternative embodiment of the cavity forming tip 44. The cavity forming tip 44 illustrated in FIGS. 36-39 have the same features as described in FIG. 33. As illustrated in FIG. 36, cavity forming tip 44 has a plurality of individually formed displacement members 126A-126E, collectively referred to as 126. In addition to the displacement members 126A-126E, the cavity forming tip 44 contains a pointed member 130, illustrated as an attached trocar tip. The displacement members 126A-126E are formed in the same manner as described above. Once the displacement members are formed, the trocar tip 130 can be coupled, through chemical fastening mechanisms or other known fastening mechanisms known to one of skill in the art, to at least one of the displacement members 126A-126E. In the closed position, each of the displacement members 126A-126E folds behind the trocar tip 130, see FIG. 38. FIGS. 40-43 illustrate an alternative embodiment of the cavity forming tip 44. The cavity forming tip 44 illustrated in FIGS. 40-43 have the same features as described in FIGS. 36 and 38, but differ in that the trocar tip 130 is integrally formed as part of the cavity forming tip 44. The displacement members are formed by splitting the cavity forming tip 44 with the trocar tip 130 and then shaping each of the displacement members. In this configuration, one of the displacement members, 126C, contains a pointed end 130, see FIG. 40. Because the trocar tip 130 is integrally formed with the tip and the displacement members 126A-126E are formed by splitting and shaping each member into a desired configuration, the resulting length of the displacement members 126A-126E are not equal and contain partially rounded ends. As illustrated in FIG. 41, when in the closed position, the length of displacement member 126C is larger than the displacement members 126B and 126A. The length of the displacement member 126B is larger than the displacement member 126A.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A device for creating cavities or void spaces within a tissue or organ comprising:
   an insertable member receiving structure containing a proximal end, a distal end, and a main body therebetween, said insertable member receiving structure main body containing a longitudinal bore sized and shaped to receive an insertable member;
   a first insertable member rotatably coupleable to said insertable member receiving structure, said first insertable member containing a proximal end, a distal end, and a first insertable member main body extending between the proximal end and the distal end, said distal end having a tip with a plurality of displacement members, a necked down section between said tip and said first insertable member main body, each displacement member of said plurality of displacement members having a planar shape, said plurality of displacement members being adapted for traversing between a cavity forming, open configuration and a non-cavity forming, closed configuration by angularly deforming said displacement members respective to a longitudinal axis of said first insertable member main body about a pivotal axis, wherein said pivotal axis is perpendicular to a plane defined by said planar shape of each displacement member, wherein said angular deformation is enabled by said necked down section;
   wherein said displacement members have a spring characteristic allowing said displacement members to traverse from a cavity forming, opened configuration of a substantially planar fan-shaped configuration with an inner edge of one displacement member of said plurality of displacement members overlaying and proximate an opposite, outer edge of an adjacent displacement member of said plurality of displacement members forming a continuous blade shape to a non-cavity forming, closed configuration, wherein each of said displacement members are placed in collapsed linear alignment overlaying one another to form a single member,
   whereby rotation of said first insertable member displaces cells, cellular debris, or tissue components from a body organ or tissue thereby forming a void or cavity region therein.

2. The device for creating cavities or void spaces within a tissue or organ according to claim 1, wherein said insertable member receiving structure contains a handle.

3. The device for creating cavities or void spaces within a tissue or organ according to claim 2, wherein said handle is ergonomically shaped.

4. The device for creating cavities or void spaces within a tissue or organ according to claim 1, wherein said insertable member receiving structure contains a tissue or organ engaging tip.

5. The device for creating cavities or void spaces within a tissue or organ according to claim 4, wherein said tissue or organ engaging tip is a multi-faceted, triple crown cannulated tip.

6. The device for creating cavities or void spaces within a tissue or organ according to claim 1, wherein said insertable member receiving structure main body contains one or more stabilizing members.

7. The device for creating cavities or void spaces within a tissue or organ according to claim 1, wherein said first insertable member further contains a device for gripping and aiding in rotating said first insertable member.

8. The device for creating cavities or void spaces within a tissue or organ according to claim 7, wherein said device is a knob.

9. The device for creating cavities or void spaces within a tissue or organ according to claim 1, wherein said displacement members are made of superelastic alloys which can be constrained into a first shape and then deployed to a second shape without experiencing plastic deformity.

10. The device for creating cavities or void spaces within a tissue or organ according to claim 1, wherein said displacement members are made of nitinol.

11. The device for creating cavities or void spaces within a tissue or organ according to claim 1, wherein said displacement members contain curved portions with generally rounded terminal ends.

12. The device for creating cavities or void spaces within a tissue or organ according to claim 1, wherein proximal ends of each of said displacement members are collectively coupled to said insertable member main body at said necked down section.

13. The device for creating cavities or void spaces within a tissue or organ according to claim 1, wherein at least one said displacement member includes at least one edge angled to form a V-shape body.

14. The device for creating cavities or void spaces within a tissue or organ according to claim 12, wherein said displacement members are arranged to expand into a cavity forming position independently whereby said first or second displacement members expand prior to said second or first displacement member.

15. The device for creating cavities or void spaces within a tissue or organ according to claim 12, wherein said displacement members are arranged to expand into a cavity forming position simultaneously.

16. The device for creating cavities or void spaces within a tissue or organ according to claim 1, wherein a center member of said plurality of displacement members is formed having a pointed distal end.

17. The device for creating cavities or void spaces within a tissue or organ according to claim 1, comprising at least three displacement members.

18. The device for creating cavities or void spaces within a tissue or organ according to claim 17 wherein each of said displacement members is the same or similarly sized, whereby in the closed position, all said displacement members align forming an edge that is generally linear.

19. The device for creating cavities or void spaces within a tissue or organ according to claim 17, wherein at least one displacement member includes a pointed member at the distal end.

20. The device for creating cavities or void spaces within a tissue or organ according to claim 19, wherein the lengths of at least one of said displacement members is smaller than the length of at least one second displacement member.

21. The device for creating cavities or void spaces within a tissue or organ according to claim 1, said plurality of displacement members include at least one of:
  a pointed member extending forward of a central displacement member of said displacement members,
  a pointed member extending forward of a central displacement member of said displacement members, wherein said pointed member is an attached trocar tip,
  wherein each of said displacement members are placed in collapsed linear alignment to form a single member,
  wherein each of said displacement members are placed in collapsed linear alignment to form a single member and a pointed member extending forward of a central displacement member of said displacement members,
  wherein each of said displacement members are placed in collapsed linear alignment to form an edge that is generally linear, and
  wherein each of said displacement members are placed in collapsed linear alignment to form an edge that is generally linear and a pointed member extending forward of a central displacement member of said displacement members.

22. The device for creating cavities or void spaces within a tissue or organ according to claim 1, said cavity forming tip configured in at least one of:
  wherein each of said displacement members are placed in collapsed linear alignment to form a single member, and
  wherein each of said displacement members are placed in collapsed linear alignment to form an edge that is generally linear.

23. A system for creating cavities or void spaces within a tissue or organ comprising:
  an insertable member receiving structure containing a proximal end, a distal end, and a main body therebetween, said insertable member receiving structure main body containing a longitudinal bore sized and shaped to receive an insertable member;
  at least one first insertable member rotatably coupleable to said insertable member receiving structure, said first insertable member containing a proximal end, a distal end, and a first insertable member main body extending between the proximal end and the distal end, said distal end having a tip with a plurality of displacement members, a necked down section between said tip and said first insertable member main body, each displacement member of said plurality of displacement members having a planar shape, said plurality of displacement members being adapted for traversing between a cavity forming position and a non-cavity forming position by angularly deforming said displacement members respective to a longitudinal axis of said first insertable member main body about a pivotal axis, wherein said pivotal axis is perpendicular to a plane defined by said planar shape of each displacement member, wherein said angular deformation is enabled by said necked down section,
  wherein said displacement members have a spring characteristic allowing said displacement members to traverse from a cavity forming, opened configuration of a substantially planar fan-shaped configuration with an inner edge of one displacement member of said plurality of displacement members overlaying and proximate an opposite, outer edge of an adjacent displacement member of said plurality of displacement members forming a continuous blade shape to a non-cavity forming position, closed configuration, wherein each of said displacement members are placed in collapsed linear alignment overlaying one another to form a single member; and
  a second insertable member having a proximal end having a gripping member, a distal end containing a pointed end for inserting into a hard surface, and a second insertable member main body traversing between said distal end and said proximal end, said second insertable member being sized and shaped to be insertable and traversable within said lumen of said insertable member receiving structure;
  whereby rotation of said first insertable member displaces cells, cellular debris, or tissue components from a body organ or tissue to form a void or cavity therein.

24. A kit for creating cavities or void spaces within a tissue or organ comprising: an insertable member receiving structure containing a proximal end, a distal end, and a main body therebetween, said insertable member receiving structure main body containing a longitudinal bore sized and shaped to receive an insertable member;
  at least one first insertable member rotatably coupleable to said insertable member receiving structure, said first insertable member containing a proximal end, a distal end, and a first insertable member main body extending between the proximal end and the distal end, said distal end having a tip with a plurality of displacement members, a necked down section between said tip and said first insertable member main body, each displacement member of said plurality of displacement members having a planar shape, said plurality of displacement members being adapted for traversing between a cavity forming position and a non-cavity forming position by angularly deforming said displacement members respective to a longitudinal axis of said first insertable member main body about a pivotal axis, wherein said pivotal axis is perpendicular to a plane defined by said planar shape of each displacement member, wherein said angular deformation is enabled by said necked down section,
  wherein said displacement members have a spring characteristic allowing said displacement members to traverse from a cavity forming, opened configuration of a substantially planar fan-shaped configuration with an inner edge of one displacement member of said plurality of displacement members overlaying and proximate an opposite, outer edge of an adjacent displacement member of said plurality of displacement members forming a continuous blade shape to a non-cavity forming position, closed configuration, wherein each of said displacement members are placed in collapsed linear alignment overlaying one another to form a single member; and
  a second insertable member having a proximal end having a gripping member, a distal end containing a pointed end for inserting into a hard surface, and a second insertable member main body traversing between said distal end and said proximal end, said second insertable member being sized and shaped to be insertable and traversable within said lumen of said insertable member receiving structure;

whereby rotation of said first insertable member displaces cells, cellular debris, or tissue components from a body organ or tissue to form a void or cavity therein.

25. The kit for creating cavities or void spaces within a tissue or organ according to claim 24, further including a plurality of said first insertable members each having at least one of differently sized and shaped displacement members.

* * * * *